(12) United States Patent
Pittet et al.

(10) Patent No.: US 9,084,715 B2
(45) Date of Patent: Jul. 21, 2015

(54) PORT DEVICE

(75) Inventors: Michel Pittet, Aumont (CH); Caroline Ansermet, Denges (CH); Bastien Ecabert, Bussigny (CH); Alain Cozian, Les Clees (CH)

(73) Assignee: B. BRAUN MELSUNGEN AG, Melsungen (DE)

( * ) Notice: Subject to any disclaimer, the term of this patent is extended or adjusted under 35 U.S.C. 154(b) by 266 days.

(21) Appl. No.: 13/695,178

(22) PCT Filed: May 2, 2011

(86) PCT No.: PCT/EP2011/056960
§ 371 (c)(1),
(2), (4) Date: Oct. 29, 2012

(87) PCT Pub. No.: WO2011/141316
PCT Pub. Date: Nov. 17, 2011

(65) Prior Publication Data
US 2013/0049356 A1    Feb. 28, 2013

(30) Foreign Application Priority Data

May 10, 2010   (EP) ..................................... 10162382

(51) Int. Cl.
*A61B 19/00*     (2006.01)
*A61J 1/14*      (2006.01)
(Continued)

(52) U.S. Cl.
CPC .............. *A61J 1/1475* (2013.01); *A61F 5/4405* (2013.01); *A61J 1/10* (2013.01); *A61J 1/1462* (2013.01)

(58) Field of Classification Search
CPC ......... A61J 1/10; A61J 1/1475; A61J 1/1462; A61F 5/4405

USPC ........ 604/4.01, 6.16, 905, 262, 403–416, 33, 604/332; 383/200, 202, 38, 42, 59, 78, 383/93–94; 206/461, 466; 220/62.11, 220/62.12, 62.21, 660, 661
See application file for complete search history.

(56) References Cited

U.S. PATENT DOCUMENTS 5,941,866 A * 8/1999 Niedospial, Jr. .............. 604/408
2007/0027437 A1* 2/2007 Burg et al. ..................... 604/415
(Continued)

FOREIGN PATENT DOCUMENTS

CH          677093 A5    4/1991
DE       20200689 U1    7/2003
(Continued)

*Primary Examiner* — Philip R Wiest
*Assistant Examiner* — Ariana Zimbouski
(74) *Attorney, Agent, or Firm* — Clements Bernard PLLC; Gregory N. Clements

(57) ABSTRACT

A port device (10) for a fluid storage bag (46) comprises a housing (12) having a bottom wall (14) and opposing sidewalls (16, 18), and a connective opening (20) in said housing (12) opposite to said bottom wall (14). The connective opening (20) is adapted to be connected with said fluid storage bag (46) and has an elongate surface area shaped by a wide center portion (22) and peaked longitudinally opposing ends (24). A port device (10) further comprises at least one access port (26) in said bottom wall (14) adapted to communicate with the interior of said fluid storage bag (46) through said connective opening (20). In order to be fixable to the fluid storage bag (46) in a safe and easy manner, said port device (10) further comprises at least one bridge element (32) supporting said sidewalls (16, 18) and oriented transversely to the longitudinal direction (34).

7 Claims, 3 Drawing Sheets

Figure 1:
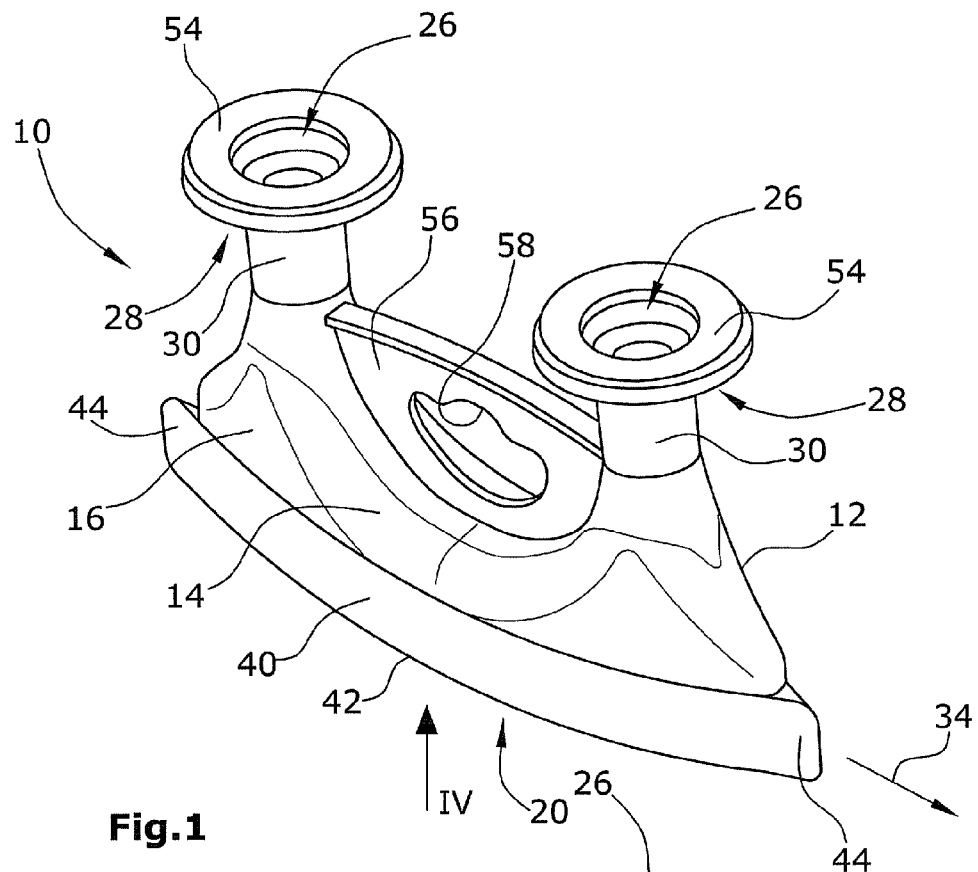

(51) Int. Cl.
*A61F 5/44* (2006.01)
*A61J 1/10* (2006.01)

(56) References Cited

U.S. PATENT DOCUMENTS

2008/0140047 A1* 6/2008 Young ........................... 604/408
2009/0270832 A1 10/2009 Vancaillie et al.
2010/0211033 A1* 8/2010 Blum ........................... 604/335

FOREIGN PATENT DOCUMENTS

| EP | 0083778 A2 | 7/1983 |
| WO | 02085111 A1 | 10/2002 |
| WO | 03031280 A1 | 4/2003 |

* cited by examiner

PORT DEVICE

The invention refers to a port device for a fluid storage bag.

Fluid storage bags are used in the medical field for storage of blood or other liquid, which is to be transfused to a patient. The fluid storage bags are typically made of a flexible material. A port device functions as an adapter for connecting a transfusion hose to the storage bag in order to fill the bag or to conduct fluid from the storage bag to a needle or catheter and into the patient.

EP 0 083 778 A2 and DE 202 00 689 U1 disclose port devices comprising a housing having a bottom wall and opposing sidewalls, and comprising a connective opening in said housing opposite to said bottom wall. The connective opening is adapted to be connected with said fluid storage bag and has an elongate surface area shaped by a wide center portion and peaked longitudinally opposing ends. At least one access port is provided in said bottom wall for communicating with the interior of the fluid storage bag through said connective opening. The wide center portion and the peaked longitudinally opposing ends enable the abutting portions of the storage bag to smoothly lie against the port device such that the port device and the storage bag can be welded smoothly without any remaining wrinkles in the storage bag or without any remaining edges or projections that might damage the storage bag. A wide center portion of the connective opening is necessary in order to allow for a certain amount of volume to flow through the port device.

An object of the invention is to provide a port device, which can be fixed to the fluid storage bag in a safe and easy manner.

The port device of the invention is defined by the features in independent claim 1.

Accordingly, the port device comprises at least one bridge element supporting said sidewalls and oriented transversely to the longitudinal direction. The longitudinal direction is defined by the elongate surface area and its longitudinally opposing ends. The bridge element supports the sidewalls against a force, which acts on the sidewalls in a transverse direction. Such force is typically exerted on the port device sidewalls when the fluid storage bag is being attached to the port device. Typically, portions of the fluid storage bag are welded or glued to outer portions of the sidewalls. When the storage bag is pressed onto the sidewalls in a transverse direction, breakage or damage of the port device is avoided by the bridge element. The bridge element allows for a wide center portion and thus for a large flow of liquid through the connective opening.

The bridge element has an undercut edge being spaced from the bottom wall in order to define a fluid passage between the bridge element and the bottom wall. Thereby, the bridge element supports the sidewalls without disturbing a flow of liquid passing through the connective opening and through the fluid passage.

Each said sidewall may form a welding portion on the outside of said housing. Each welding portion may have a circular segment shaped edge, which borders the surface area of the connective opening. The depth extensions of the welding portions may be parallel to each other. This results in an advantageous welding area for attaching the fluid storage bag. The circular segment shaped edge allows for a wide center portion and a smooth transition to the peaked longitudinally opposing ends and thereby allows for a smooth continuous shape of the welding portion for attaching the storage bag. The parallel depth extensions of the welding portions enable the fluid storage bag to be pressed against the welding portion from both sides simultaneously in a transverse direction, whereby the bridge element avoids breakage of the port device.

According to an embodiment, the port device further comprises noses outwardly extending from the welding portions in the longitudinal direction at the peaked opposing ends of the connective opening. The noses at each peaked opposing end allow for a sharp peak and thereby for a smooth transition between the port device and the fluid storage bag. Consequently, the storage bag can be welded to the port device without any remaining openings through which fluid might leak.

According to a further embodiment, the bottom wall and the sidewalls form a funnel tapered to each access port in order to allow for a smooth continuous transition between the connective opening and the access port without any resistance for the fluid. In particular, in case of blood flowing through the port device, resistant geometries for the blood flow would be highly critical due to coagulation of blood particles, which would endanger a patient's health or even life.

Advantageously, the port device comprises at least two adjacent access ports, wherein the bottom wall circumscribes a semi-circle between the adjacent access ports in side view and wherein the closest distance between the bottom wall and the connective opening is halfway between the adjacent access ports. Adjacent access ports are advantageous in different applications of a fluid storage bag. E.g., one access port could be used for conducting the fluid to the patient and the other access port could be used in order to refill the storage bag or to introduce a specific medication or other substance into the storage bag during an infusion. The semi-circle-shape with the closest distance between the bottom wall and the connective opening halfway between the adjacent access ports is advantageous as such shape avoids critical resistant geometries, which might disturb the fluid flow. This geometry is in particular advantageous in combination with the bottom and sidewalls forming a funnel tapered to each access port.

According to a further embodiment, each access port is formed at a distal end of a cylindrical neck extending from the housing. The length of the neck should at least be one centimeter such that the neck can be grasped easily with the fingers of a medical practitioner, who for example needs to attach a hose to the access port or inject a substance into an access port. Injection of a substance into the access port would typically be conducted with a syringe and is safer for the medical practitioner, if the distal end of the cylindrical neck comprises a circular flange having an outer diameter, which is larger than the outer diameter of the circular neck. The circular flange projects outwardly from the circular neck and forms a shield protecting the fingers of a medical practitioner from being accidentally pierced by a needle of a syringe when a substance is to be injected into an access port.

In addition, the length of the housing, i.e. the distance between each access port and the connective opening should be sufficient to avoid that a needle which is introduced into the access port pierces the fluid storage bag or a patient or medical practitioner. This is in particular important, for example, when adding cytostatica to the bag. The length should at least be 3 centimeters and, preferably, be 4 centimeters. Thus, additional user safety is achieved by employing the rigid housing as a needle shield for avoiding accidental needle sticks. Also, a funnel shape of the bottom and sidewalls being tapered to each access port additionally avoids accidental needle sticks into the housing upon introduction of a needle into the access port due to the widening diameter of the neck and housing.

According to an advantageous embodiment, the cylindrical necks of adjacent access ports are connected with each other by a connecting bar, which defines a mounting portion for the port device. Such connecting bar stabilizes the port device and in particular the adjacent cylindrical necks and allows for an easy mounting of the port device and the attached fluid storage bag. In particular, such mounting portion would be provided in the balance point resulting in stable and safe mounting of the storage bag or for safe and easy grasping of the storage bag for transportation purposes.

Figure 2:
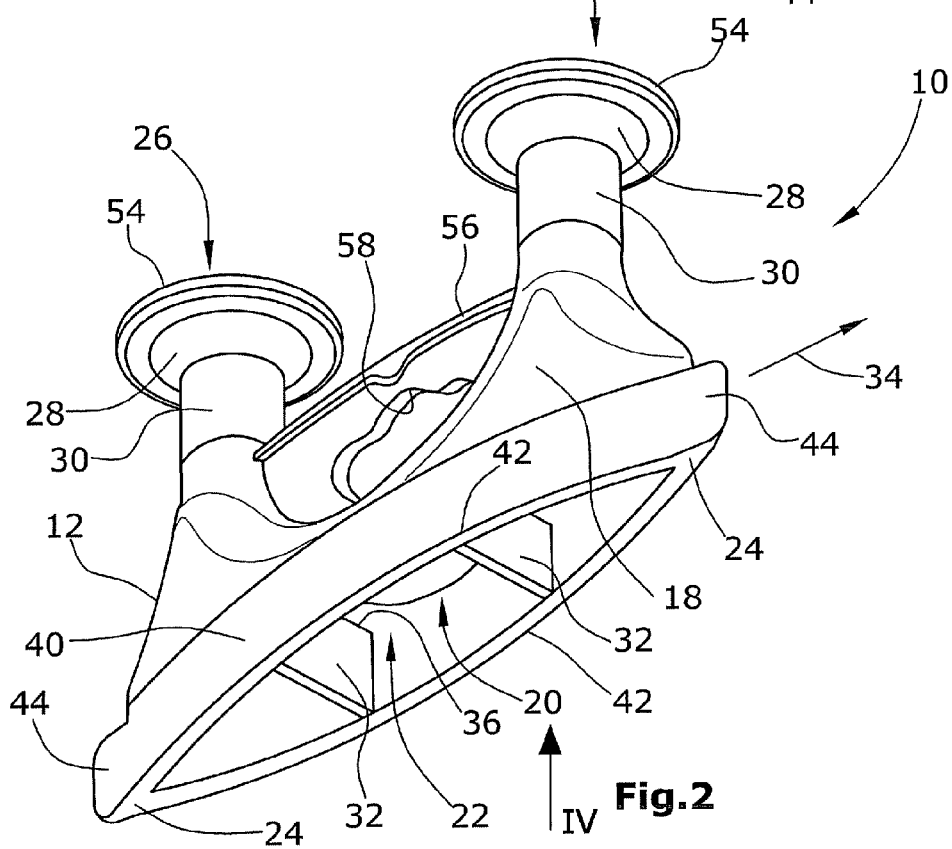
Figure 3:
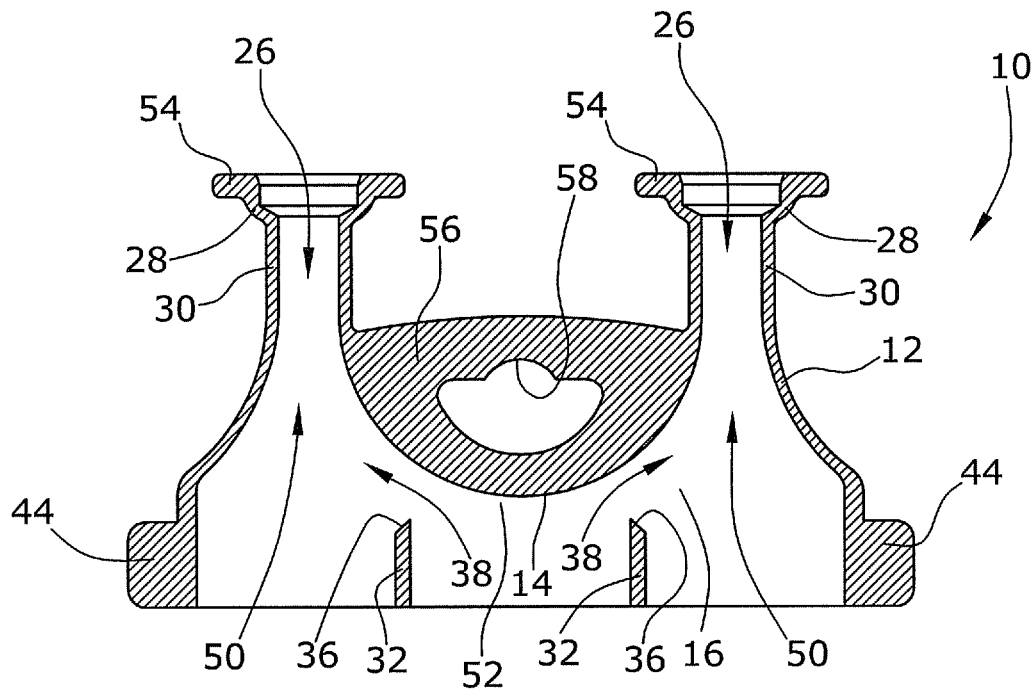
Figure 4:
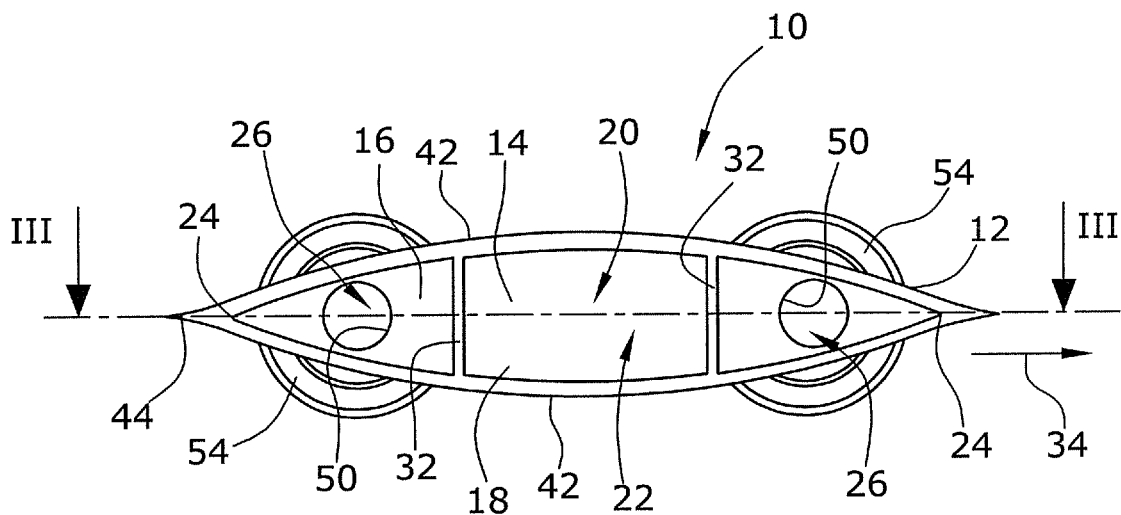
Figure 5:
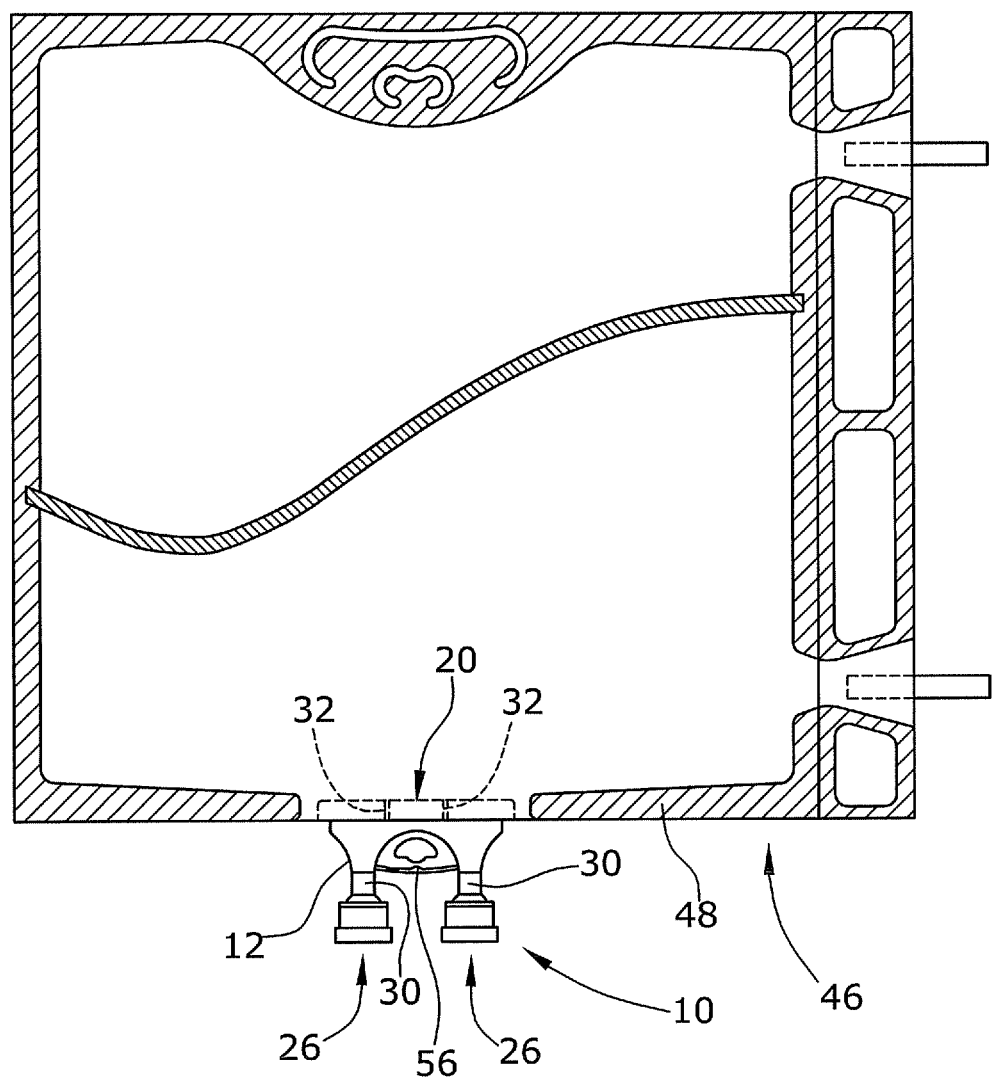

In the following, an embodiment of the invention will be described with reference to the drawings in which FIG. 1 shows a three-dimensional lower view of the port device, FIG. 2 shows a three-dimensional upper view of the port device, FIG. 3 shows a longitudinal sectional view according to line III-III in FIG. 4, FIG. 4 shows an upper view according to the arrow IV in FIGS. 1 and 2 and FIG. 5 shows a longitudinal sectional view of the port device welded to a fluid storage bag.

The port device 10 comprises a housing 12 having a bottom wall 14 and opposing sidewalls 16 and 18. A connective opening 20 is formed in the housing opposite to the bottom wall 14. The connective opening 20 has, as best shown in FIG. 4, an elongate surface area, which is shaped by a wide center portion 22, and peaked longitudinally opposing ends 24. Two access ports 26 are formed in the bottom wall 14 at respective distal ends 28 of cylindrical necks 30 extending from the housing 12. Consequently, the access ports 26 and the connective opening 20 are formed on opposite sides of the housing 12.

Two bridge elements 32 are integrally provided between the housing sidewalls 16 and 18, thereby supporting said sidewalls 16, 18. The bridge elements 32 are positioned in the wide center portion 22 of connective opening 20 and are oriented transversely with respect to the longitudinal direction 34. Each bridge element 32 has an undercut edge 36, which is spaced from the bottom wall 14, thereby defining a fluid passage 38 between each bridge element 32, the sidewalls 16, 18 and the bottom wall 14. The fluid passage 38 extends from the connective opening 20 through the housing 12 to each access board 26 and vice versa in order to allow for fluid communication between the connective opening 20 and each access port 26.

On the outside of the housing 12, each sidewall 16, 18 forms a welding portion 40. Each welding portion has a circular segment shaped edge 42, which borders the surface area of the connective opening 20. The depth extensions of the welding portions 40 are parallel to each other. The depth extensions are oriented in parallel to the cylindrical necks 30 and transversely to the longitudinal direction 34. On each longitudinally opposing end 24, projecting noses 44 are formed. Each nose 44 extends outwardly from the welding portions 40 in the longitudinal direction. Thereby, the noses 44 serve as extensions of the welding portions to be contacted by the fluid storage bag 46 as shown in FIG. 5 in order to weld outer rims 48 of the fluid storage bag 46 to the welding portions 30. Each nose 44 forms an outwardly extending longitudinally projecting sharp edge such that the storage bag 46 can be welded to the port device 10 without any remaining leakage openings.

As best shown in FIGS. 3 and 4, the bottom wall 14 and both sidewalls 16 and 18 form two funnels 50, each funnel being tapered to one access port 26. The bottom wall circumscribes a semi-circle 52, as best shown in FIG. 3, between the adjacent access ports 26, wherein the closest distance between the bottom wall 14 and the connective opening 20 is halfway between the adjacent access ports with respect to the longitudinal direction 34. The semi-circle shape in side view of the bottom wall 14 is part of the funnel geometry such that a continuous and evenly inclined structure is formed as fluid passage 38 without any resistant projections, which could disturb the flow of fluid or liquid.

The length of each cylindrical neck 30 is approximately 1 cm such that each cylindrical neck 30 can be easily grasped by a user. A circular flange 54 at the distal end of each cylindrical neck serves as a protective shield for the fingers of a user grasping the port device on a cylindrical neck 30.

A connecting bar 56 connects the cylindrical necks 30 with each other. The connecting bar 56 is integrally formed with the port device and defines a mounting portion 58. The mounting portion 58 is part of a through hole through a disk-like structure, which is bordered by the connecting bar 56 and the semi-circle 52 of the bottom wall 14. The connecting bar 56 and the disk-like structure increase the stability and rigidity of the port device and provide for a safe and stable way of mounting the port device at the mounting portion 58.

The invention claimed is:

1. Port device (10) for a fluid storage bag (46) comprising
a housing (12) having a bottom wall (14) and opposing sidewalls (16, 18),
a connective opening (20) in said housing opposite to said bottom wall (14), the connective opening (20) adapted to be connected with said fluid storage bag (46) and having an elongate surface area shaped by a wide center portion (22) and peaked longitudinally opposing ends (24),
at least one access port (26) in said bottom wall (14) adapted to communicate with the interior of said fluid storage bag (46) through said connective opening (20), and
at least one bridge element (32) supporting said sidewalls (16, 18) and oriented transversely to the longitudinal direction (34),
characterized in that
said bridge element (32) has an undercut edge (36) spaced from said bottom wall (14) defining a fluid passage (38) between said bridge element (32) and said bottom wall (14), characterized in that said bottom wall (14) and said sidewalls (16, 18) form a funnel (50) tapered to each said access port (26),
said port device (10) comprises at least two adjacent access ports (26), said bottom wall (14) circumscribing a semi-circle (52) between said adjacent access ports (26) in side view, wherein the closest distance between said bottom wall (14) and said connective opening (20) is halfway between said adjacent access ports (26).

2. Port device (10) according to claim 1, characterized in that each said sidewall (16, 18) forms a welding portion (40) on the outside of said housing (12), each welding portion (40) having a circular segment shaped edge (42) bordering the surface area of said connective opening (20), the depth extensions of said welding portions (40) being parallel to each other.

3. Port device (10) according to claim 2, characterized in that said port device (10) further comprises noses (44) outwardly extending from said welding portions (40) in the longitudinal direction (34) at said peaked opposing ends (24) of said connective opening (20).

4. Port device (1) according to claim 1, characterized in that cylindrical necks (30) of adjacent access ports are connected with each other by a connecting bar (56) defining a mounting portion (58) for said port device (10).

5. Port device (10) according to claim 1, characterized in that each access port (26) is formed at a distal end (28) of a cylindrical neck (30) extending from said housing (12).

6. Port device (10) according to claim 5, characterized in that the length of said cylindrical neck (30) is at least 1 cm.

7. Port device (10) according to claim 5, characterized in that the distal end (28) of said cylindrical neck (30) comprises a circular flange (54) having an outer diameter which is larger than the outer diameter of said circular neck.

\* \* \* \* \*